United States Patent [19]

Yoshioka

[11] Patent Number: 5,227,472
[45] Date of Patent: Jul. 13, 1993

[54] ANTIGEN FOR PRODUCING AN ANTIBODY AGAINST MHPG

[75] Inventor: Masanori Yoshioka, Yawata, Japan

[73] Assignee: Daiichi Radioisotope Laboratories, Ltd., Tokyo, Japan

[21] Appl. No.: 485,531

[22] Filed: Feb. 27, 1990

[30] Foreign Application Priority Data

Feb. 28, 1989 [JP] Japan .................................. 1-47148

[51] Int. Cl.$^5$ ........................ C07K 15/06; C08H 1/00
[52] U.S. Cl. .................................... 530/403; 530/362; 530/363; 530/402; 530/406; 424/88
[58] Field of Search ............... 530/362, 402, 406, 363, 530/403; 424/88

[56] References Cited

U.S. PATENT DOCUMENTS 5,145,791  9/1992  Zeitvogel et al. .................. 530/363

OTHER PUBLICATIONS

Niklasson et al., Biol. Psychiatry (USA) vol. 19 (8) pp. 1183–1206 (1984) (abstract).
Keeton et al., *Science*, 211: 586–588 (1981).

*Primary Examiner*—Jeffrey E. Russel
*Attorney, Agent, or Firm*—Bacon & Thomas

[57] ABSTRACT

An antigen containing 3-methoxy-4-hydroxyphenylethylene glycol and represented by formula (I):

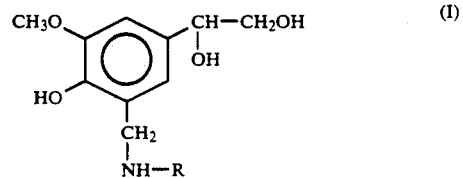

(wherein R-NH is the residue of a polypeptide carrier R-NH$_2$), and a method of producing an antibody to 3-methoxy-4-hydroxyphenylethylene glycol, characterized in that the method comprises immunizing an animal by using the antigen containing 3-methoxy-4-hydroxyphenylethylene glycol. The MHPG antigen of the present invention is capable of producing an MHPG antibody of high specificity. This antibody enables a precise determination of MHPG in specimens such as body fluid.

3 Claims, 4 Drawing Sheets

ANTIGEN FOR PRODUCING AN ANTIBODY AGAINST MHPG

BACKGROUND OF THE INVENTION

The present invention relates to a method of producing an antibody to 3-methoxy-4-hydroxyphenylethylene glycol (abbreviated as MHPG hereinafter) which is useful for the measurement of MHPG, an antigen used in the production of the antibody and a method of producing the antigen.

MHPG is a neutral metabolite of norepinephrine and epinephrine, which are adrenal medullary hormones and serve as neurotransmitters of the sympathetic nerve and the central nerve. Measurement of the increase or decrease of MHPG in body fluid is very important for elucidating the transmission function of these information substances.

More particularly, the concentration level of MHPG in the blood or the cerebrospinal fluid is considered to reflect the norepinephrine level in the brain. The measurement of MHPG is also important for the diagnosis of diseases such as melancholia, malignant subarachnoid hemorrhage, and so on, because these diseases are inclined to cause an increase in MHPG levels.

Hitherto, for measuring MHPG levels, gas chromatography, mass spectrometry, high-performance liquid chromatography or the like have been employed. These methods, however, are cumbersome in operation, and only a few specimens can be measured at a time.

Meanwhile, immunological measurement is very capable of rapidly and simply measuring many specimens at a time. This approach, however, requires preparing antibodies and antigens.

A method of preparing an MHPG antigen and an antibody to MHPG has been reported by T. Keeton et al (Science, 211, 586-588, 1981) which comprises reacting 6-bromocaproic acid with MHPG to modify the hydroxyl group at the 4-position of MHPG to $-O-(CH_2)_5-COOH$, bonding a carrier protein to this carboxyl group via a carbodiimide method to prepare an antigen, and immunizing an animal with the antigen to obtain an antibody.

The thus-formed antibody is not cross-reacted with catecholamine or acid metabolites, but is weakly cross-reacted with 3,4-dihydroxyphenylethylene glycol.

SUMMARY OF THE INVENTION

In consideration of the above situation, the inventor has energetically researched a solution to the above-described problem, and, as a result, has found than an excellent MHPG antibody of high specificity can be obtained by using an MHPG antigen represented by formula (I):

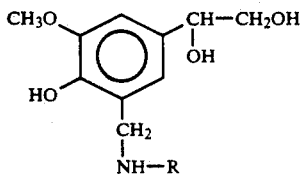

(I)

(wherein R-HN- is the residue of a polypeptide carrier R-NH$_2$), which is obtained by bonding a polypeptide carrier R-NH$_2$ at the 5-position of MHPG through the amino group thereof by a Mannich reaction using formaldehyde. The present invention has been achieved based on this finding.

DETAILED DESCRIPTION OF THE PREFERRED EMBODIMENTS

Figure 1:
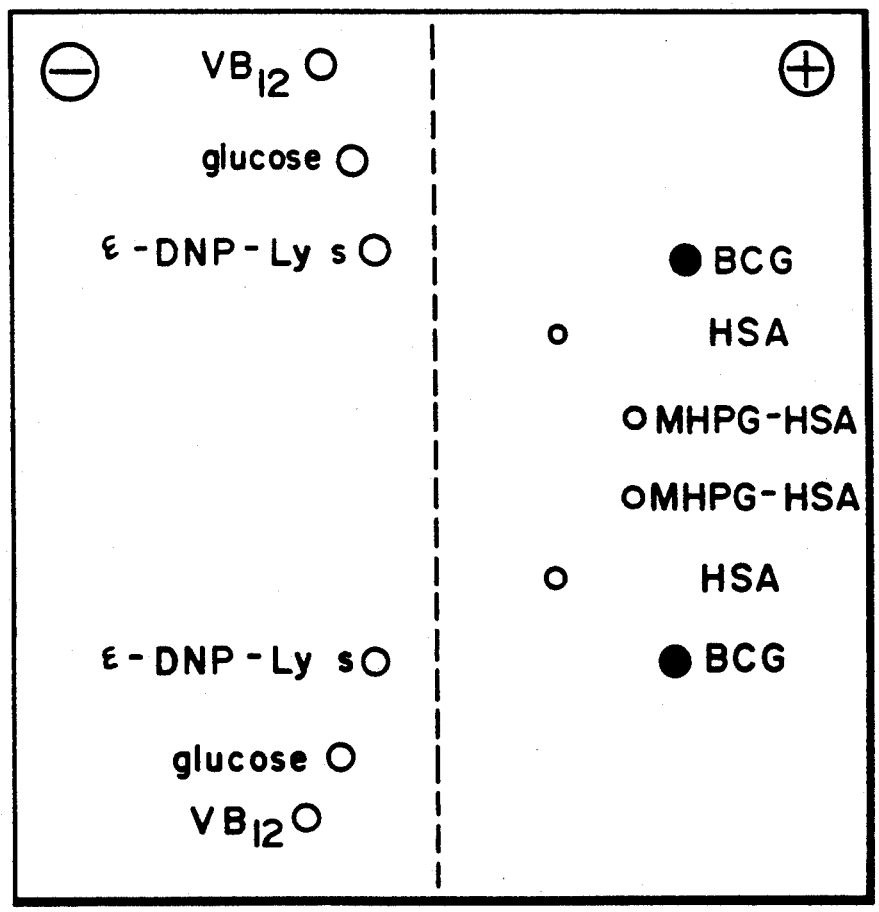
FIG. 1 is an electrophorogram of an antigen (MHPG-HSA) of the present invention.

In the present invention, an MHPG antigen of formula (I) is produced by bonding a carrier polypeptide R-NH$_2$ to MHPG by the Mannich reaction using formaldehyde.

An example of MHPG that may be used is a desalted product of a commercially available MHPG piperazine salt, which is desalted, for example, through SP-Sephadex (H type). Examples of carrier polypeptides that may be used include proteins such as human serum albumin (HSA), bovine serum albumin, globulin, bovine thyroglobulin, bovine globulin, hemocyanin, Ascaris and the like; and synthetic polypeptides such as polylysine, polylysilglutamic acid and the like.

The Mannich reaction is effected by reacting MHPG, the carrier polypeptide and formaldehyde at room temperature for 2 to 4 days. The reaction solution is dialyzed against water, diluted hydrochloric acid, and water, in this order, so that excess MHPG and formaldehyde are removed. The inner solution is freeze-dried to obtain an MHPG antigen (I).

It was confirmed, from the increase in absorbance at 280 nm of the thus-obtained MHPG antigen, that, when HSA was used as the polypeptide carrier, 8 moles of MHPG are bonded to 1 mole of HSA. Further, when the antigen is subjected to electrophoresis, the mobility toward a positive electrode is greater than that of HSA. This result indicates that the positive charge of the amino group is reduced due to the bonding of MHPG.

When an animal is immunized with the MHPG antigen (I), an antibody to MHPG is obtained. The preparation of this antibody is performed by, for example, the following method:

A W/O emulsion of the antigen (I) is prepared by using a complete Freund's adjuvant and then administered to an animal such as a mouse, rat, cow, rabbit, sheep or the like. Another W/O emulsion of the antigen (I) is prepared by using an incomplete Freund's adjuvant and additionally administered to the animal at intervals of about 1 month. A high antibody titer is observed in the serum after 4 additional administrations. The antibody titer may be measured by an EIA method, and the antibody to MHPG is obtained by collecting the serum.

The antibody-producing cells are collected from the thus-immunized animal and then subjected to cell fusion with myeloma cells to form hybridoma which is a monoclonal antibody.

The use of the antibody to MHPG obtained in the present invention enables a quantitative analysis of MHPG in a specimen using the EIA method. For example, this determination is carried out by the following method:

The antigen of the present invention is adsorbed on the sample wells in a microplate, and the antibody (antiserum) to MHPG and a sample are then added to the antigen for reaction. An alkali phosphatase-labelled second antibody is then reacted with the reaction product. After the microplate has been washed, p-nitrophenyl phosphate, which is a substrate, is added to the sample to allow an enzymatic reaction. The amount of MHPG in the specimen can be determined by measuring absorbance of the produced p-nitrophenol at 400 nm.

The MHPG antigen of the present invention enables the production of an MHPG antibody of high specificity. This antibody enables a precise determination of MHPG in a specimen such as body fluid.

The present invention will now be described with reference to the following Examples.

EXAMPLE 1

Preparation of MHPG Antigen 12 ml of an aqueous solution containing 100 mg/4 ml of MHPG hemipiperazine was placed on a column charged with SP-Sephadex (H type), and MHPG was eluted with water. The eluate was fractioned by 1.5 ml, and MHPG eluted in fractions 7 to 12 was pooled.

Separately, 100 mg of HSA was dissolved in 1 ml of 0.2-M $NaHCO_3$, and 1 ml of the pooled solution containing 0.044 mM of MHPG was then added to the HSA solution. 0.2 ml of 35% formalin was further added to the resultant mixture, and the pH value of the mixture was adjusted to 7.4. The mixture was then subjected to reaction at room temperature for 3 days in $N_2$ atmosphere under shading. The reaction solution was charged in a dialysis tube by which dialysis was performed 5 times against 1 liter of water at 4° C. while replacing water with new water at intervals of 1 hour. Dialysis was then performed agains 1 liter of 0.01-N HCl in place of water and then against water 4 times. The dialysate was then freeze-dried to obtain an MHPG antigen which was then stored at 4° C. A part of the dialysis solution was diluted and the amount of hapten bonded to the antibody was measured by measuring the absorbance at 280 nm, which revealed that 8 mole of hapten was bonded to 1 mole of HSA.

EXAMPLE 2

Electrophoresis of Antigen

1 μl of an antigen or HSA (5 mg/ml) was added to a cellulose acetate film. Glucose and Vitamin $B_{12}$ were then spotted on the film for the purpose of correcting electroendosmosis. $\epsilon$-2,4-dinitrophenyllysine ($\epsilon$-DNP-Lys) and bromocresol green (BCG) were also spotted as tracking dyes on the film. Electrophoresis was then effected in a 0.07M veronal buffer (pH 8.6) at 0.6 mA/cm for 20 minutes. After the film had been dyed with Ponceau 3R, it was destained by 1% acetic acid and then dried. The resultant electrophorogram of the spots is shown in FIG. 1.

EXAMPLE 3

Preparation of Antibody 2 mg of an antigen was dissolved in 1 ml of water, and a W/O emulsion was prepared by using 1 ml of a complete Freund's adjuvant. 0.1 ml of the thus-formed emulsion was injected to the abdominal cavity of each male BALB/c mice (5-week old) and then subjected to boosters at intervals of 1 month. For the booster, an emulsion was prepared by using an incomplete Freund's adjuvant in the same way as that described above. The tail of each mouse was cut 1 week after the administration so that blood was collected. The serum obtained was allowed to stand at 4° C. for overnight to obtain an antibody. The thus-obtained antibody was stored at −80° C.

EXAMPLE 4

Antibody Titer of Antiserum

An antigen or HSA was dissolved in a solution (PBS) containing a 0.01-M phosphate buffer (pH 7.4) and 0.15M NaCl so that the concentration of the antigen or HSA was 0.4 μg/ml. 50 μl of the thus-formed solution was charged in each of the sample wells of a microplate. After the microplate had been allowed to stand at 37° C. for 2 hours, the sample wells were washed 3 times with PBS (TPBS) containing 0.05% Tween 20. The antiserum obtained in Example 3 was diluted by TPBS and then charged in an amount of 50 μl in each of the sample wells. After shaking at 37° C. for 30 minutes, the microplate was washed once with TPBS, and 50 μl of a PBS solution of 8 μl/ml alkali phosphatase-labelled goat anti-mouse IgG was charged in each sample well, followed by shaking at 37° C. for 45 minutes.

Figure 2:
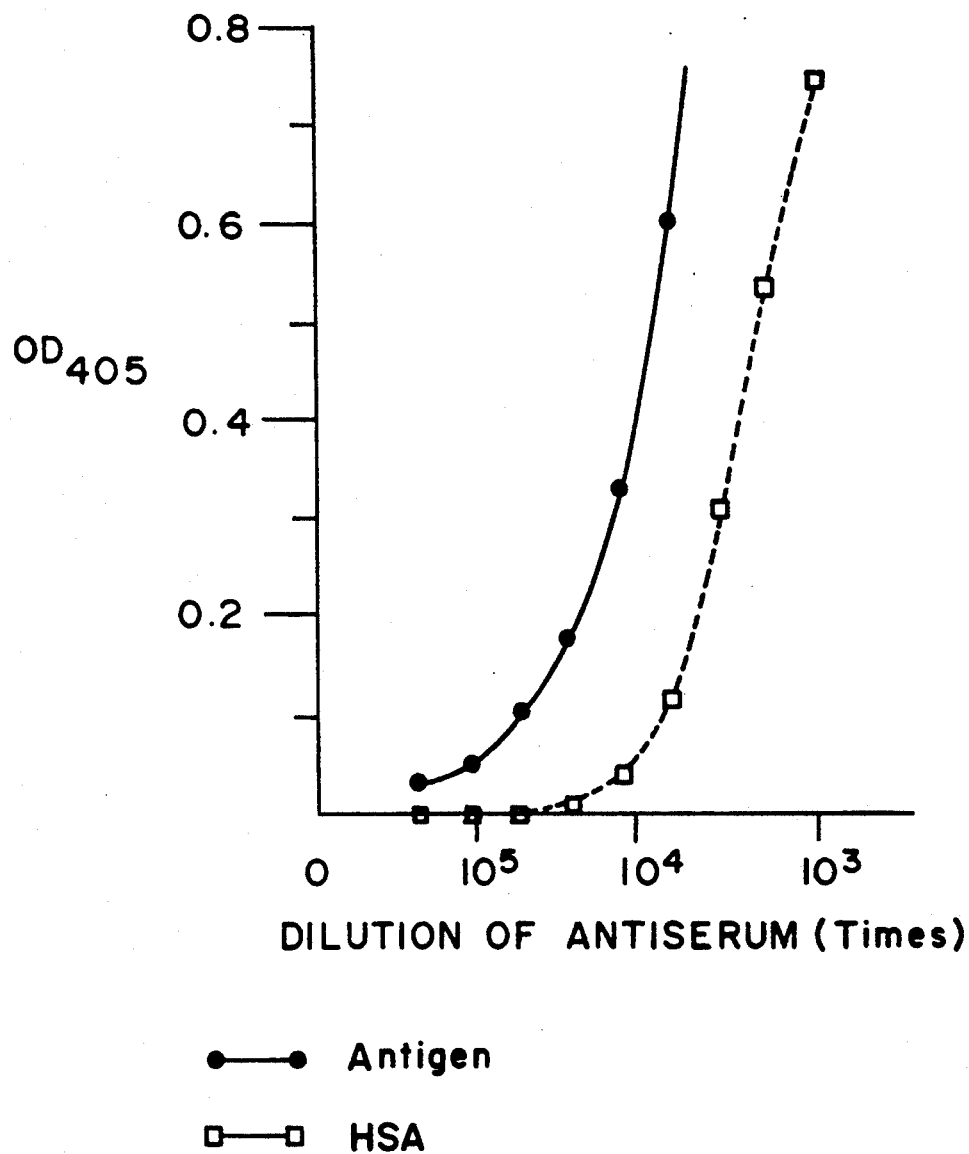
FIG. 2 is a graph which shows the results of measurement of the antibody titer of an antiserum of the present invention employing reaction between the antiserum and an antigen or HSA.

After the microplate had been washed 3 times with TPBS, 50 μl of a 100 mM $NaHCO_3$ solution of 22.4 mM p-nitrophenyl phosphate containing 1 mM of $MGCl_2$ was charged in each of the sample wells. The absorbance at a wavelength of 405 nm of the produced p-nitrophenol was measured by using an EIA reader. The results obtained are shown in FIG. 2.

EXAMPLE 5

Specificity of Antibody

Figure 3:
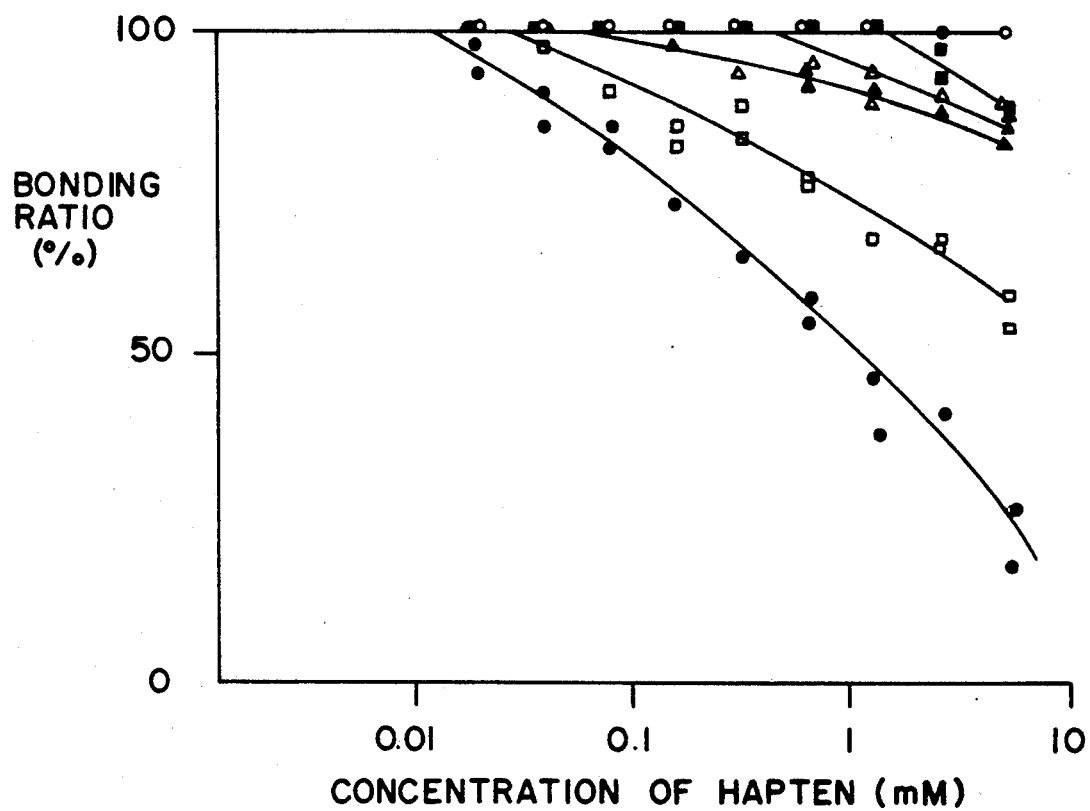
FIG. 3 is a graph which shows the affinity of an antibody of the present invention to various kinds of hapten.

25 μl of a PBS solution of 0.4 μg/ml antigen was charged in each of the sample wells of a microplate. The microplate was allowed to stand at 37° C. for 2 hours and then washed 3 times with TPBS. 12.5 μl of a diluted TPBS solution of hapten was charged in each of the sample wells, and 12.5 μl of an antiserum solution diluted 5000 times with TPBS was then charged in each sample well. After shaking at 37° C. for 30 minutes, the microplate was washed 3 times with TPBS. The same treatment as in Example 4 was then performed. The results obtained are shown in FIG. 3.

EXAMPLE 6

Formation of Calibration Curve

Figure 4:
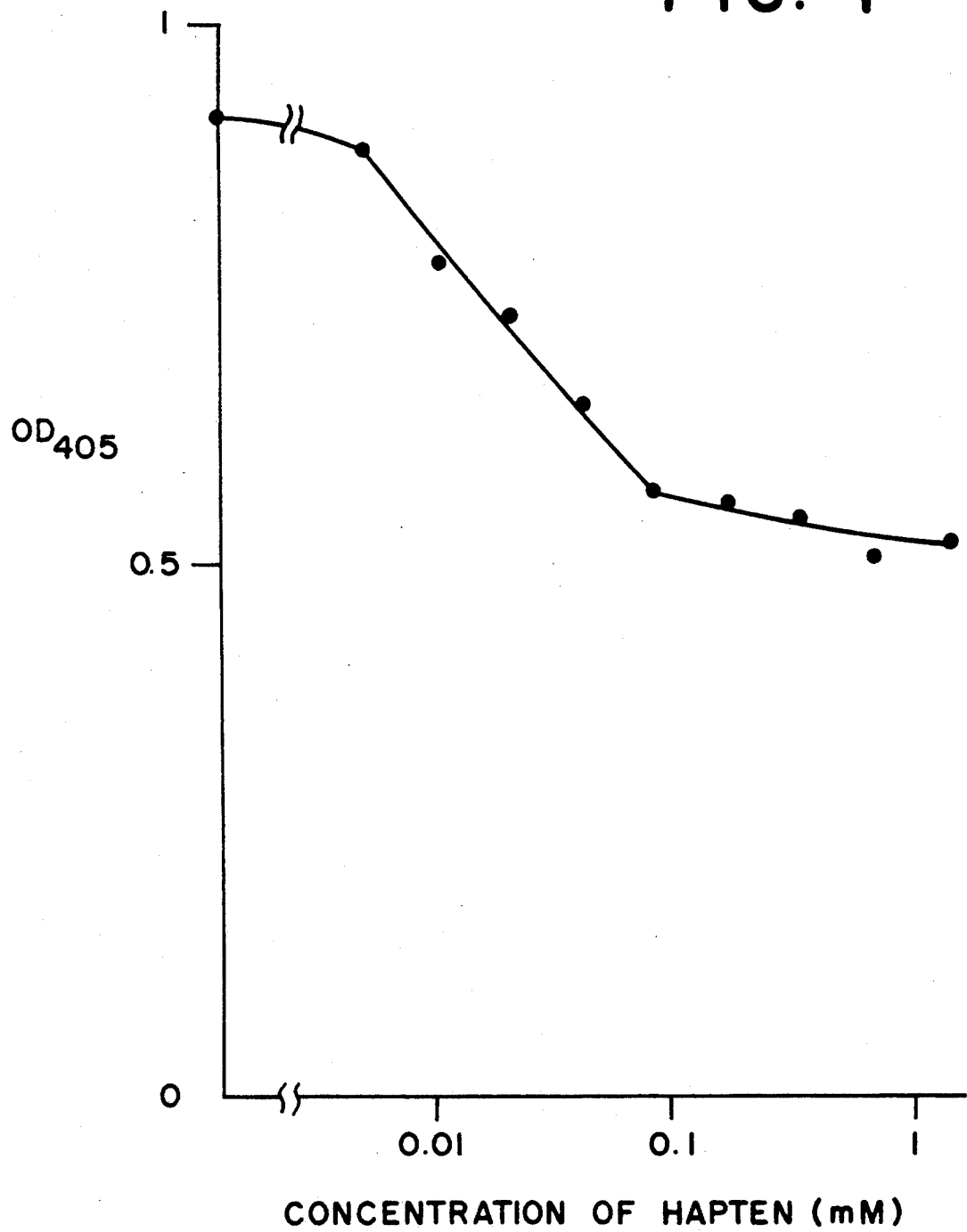
FIG. 4 is a calibration curve used for measuring MHPG utilizing an antibody of the present invention.

25 μl of a 0.01M phosphate buffer (pH 7.4, PBS) containing 0.15M NaCl of 0.4 μg/ml of the antigen of the present invention was charged in each of the sample wells of a microplate, followed by shaking at 37° C. for 2 hours. The sample wells were washed with 200 μl of a PBS solution (TPBS) containing 0.05% Tween 20. 12.5 μl of the antiserum diluted 5000 times with TPBS was added to 12.5 μl of the sample solution, and the resultant mixture was shaken at 37° C. for 30 minutes. After washing, 25 μl of 8 μg/ml alkali phosphatase-labelled goat anti-mouse IgG antibody was added to the mixture and then further shaken for 1 hour. After washing, 25 μl of 16 mM p-nitrophenyl phosphate which was dissolved in a 100 mM $NaHCO_3$ buffer (pH 9.8) containing 1 mM $MgCl_2$ was added to the mixture, followed by reaction at 37° C. The absorbance at 405 nm of p-nitrophenol produced at a period between 5 to 15 minutes after the start of the reaction was measured by using an EIA reader. The results obtained are shown in FIG. 4.

I claim:

1. An antigen containing 3-methoxy-4-hydroxyphenylethylene glycol represented by formula (I):

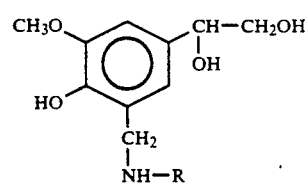

wherein R-NH is the residue of a polypeptide carrier which is selected from the group consisting of human serum albumin and bovine serum albumin.

2. An antigen according to claim 1, wherein the polypeptide carrier is human serum albumin.

3. An antigen according to claim 1, wherein the polypeptide carrier is bovine serum albumin.